United States Patent [19]

Terasawa et al.

[11] Patent Number: 5,235,400
[45] Date of Patent: Aug. 10, 1993

[54] METHOD OF AND APPARATUS FOR DETECTING DEFECT ON PHOTOMASK

[75] Inventors: Tsuneo Terasawa, Hachioji; Norio Hasegawa; Toshihiko Tanaka, both of Tokyo; Hiroshi Fukuda, Kokubunji; Toshiei Kurosaki, Katsuta, all of Japan

[73] Assignee: Hitachi, Ltd., Tokyo, Japan

[21] Appl. No.: 418,525

[22] Filed: Oct. 10, 1989

[30] Foreign Application Priority Data

Oct. 12, 1988 [JP] Japan .................. 63-254714

[51] Int. Cl.$^5$ .................. G01N 21/00; G01N 21/88
[52] U.S. Cl. .................. 356/237; 356/394; 356/239; 356/353; 250/572
[58] Field of Search .............. 356/237, 394, 239, 392, 356/430, 398, 431, 345, 349, 353, 359, 361; 430/5; 358/101, 106, 107; 250/562, 572

[56] References Cited

U.S. PATENT DOCUMENTS

| 3,972,616 | 8/1976 | Minami et al. | 356/237 |
| 4,559,603 | 12/1985 | Yoshikawa | 356/394 |
| 4,623,256 | 11/1986 | Ikenaga et al. | 356/394 |
| 4,679,938 | 7/1987 | Flamholz | 356/237 |
| 4,681,442 | 7/1987 | Wagner | 356/237 |
| 4,952,058 | 8/1990 | Noguchi et al. | 356/394 |

FOREIGN PATENT DOCUMENTS

| 5762052 | 4/1982 | Japan . |
| 58173744 | 12/1983 | Japan . |
| 6267514 | 9/1985 | Japan . |
| 0189468 | 8/1987 | Japan . |

OTHER PUBLICATIONS

SPIE, vol. 633 Optical Microlithography V(1986), pp. 138-144, Yabumoto et al.

Primary Examiner—Richard A. Rosenberger
Assistant Examiner—Hoa Q. Pham
Attorney, Agent, or Firm—Antonelli, Terry Stout & Kraus

[57] ABSTRACT

A method of and an apparatus for detecting a defect on a phase-shifting mask for use in a projection aligner in which either or both of respective intensities of transmitted and reflected light beams from the mask illuminated with light are used for detecting a defect on the mask.

18 Claims, 8 Drawing Sheets

METHOD OF AND APPARATUS FOR DETECTING DEFECT ON PHOTOMASK

BACKGROUND OF THE INVENTION

The present invention relates to a photomask used in a semiconductor fabricating apparatus, and more particularly to a method of and an apparatus for detecting a defect on a photomask, in which a portion of a light transmitting area is so formed as to shift the optical phase of illumination light.

The resolving power of a projection aligner for projecting an image of a mask pattern on an object can be improved by shifting the phase of light passing through a photomask. In order to shift the phase of light passing through the photomask, various methods have hitherto been used. For example, a thin transparent film having a thickness corresponding to the wavelength of illumination light which is used in the projection aligner is formed at a desired position on a mask substrate, as described in Japanese patent applications JP-A-58-173,744 and JP-A-57-62,052, or a predetermined surface area of a mask substrate is etched to a predetermined depth as described in a Japanese patent application JP-A-62-189,468. Further, in the example shown in a Japanese patent application JP-A-62-067,514, auxiliary patterns provided with a thin film capable of reversing the phase of illumination light are added to a mask pattern to improve the resolution of an image of the mask pattern.

In a conventional apparatus for detecting a defect on a photomask, a photomask to be inspected is illuminated by ordinary illumination means, and it is checked whether or not the light and darkness distribution on that image of a mask pattern which is formed of light passing through the photomask agrees with the light and darkness distribution on an image which has a predetermined light-transmitting area and a predetermined light-shielding area. For example, a method of comparing the light and darkness distribution on the image formed of the transmitted light from the photomask with the light and darkness distribution obtained from design data which is recorded a magnetic tape is discussed on pages 138 to 144 of SPIE, Vol. 633, Optical Microlithography V (1986).

As can be seen from the above, the conventional apparatus for detecting a defect on a photomask pays no attention to a defect in a phase-shifting mask, and cannot detect a transparent or semitransparent defect such as a transparent or semitransparent foreign substance attached to an ordinary photomask.

The term "defect" used herein includes a defect in a thin film for introducing the optical phase shifting, a defect in a chromium film for forming a light shielding area, the remainder of etching, and others.

As mentioned above, the conventional apparatus for detecting a defect on a photomask cannot detect a defect in a transparent film which is formed in a light transmitting area to act as a phase shifter.

SUMMARY OF THE INVENTION

It is accordingly an object of the present invention to provide a method of and an apparatus for detecting a defect in a transparent film formed in a light transmitting area and a transparent or semitransparent foreign substance attached to a photomask on the basis of a phase shift or intensity change in either or both of transmitted and reflected light beams from the photomask.

In order to attain the above object, a defect detecting apparatus according to the present invention is provided with means for detecting either or both of transmitted and reflected light beams from a photomask irradiated with illumination light. In a case where a defect on a photomask is detected only by the transmitted light, the photomask is illuminated with coherent or partially coherent light emitted from a light source and having a specified wavelength a to form the contour image of the defect by the transmitted light from the photomask, thereby detecting the defect. Further, in order to determine which of a light shielding area and a thin film formed in a light transmitting area for shifting the phase of illumination light has a defect, the illumination light from the light source is separated by first beam splitting means into two light beams, one of which is incident on the photomask The transmitted light from the photomask is separated by second beam splitting means into two light beams, one of which is detected by a first imaging device. The other light beam from the first beam splitting means and the other light beam from the second beam splitting means are caused to interfere, and the resultant light thus obtained is detected by a second imaging device. Binary information obtained from each of the first and second imaging devices for indicating bright and dark states is used for determining where the defect exists.

Further, in order to determine which of a light shielding area on a mask substrate and a thin film for shifting the phase of illumination light has a detect, the materials of the mask substrate and the thin film are selected so that the mask substrate has a large transmittance for the illumination light and the thin film has small transmittance. Then, the transmitted light from the photomask has three intensity levels, and thus three kinds of levels can be generated. It is determined from three kinds of levels where the defect is present.

Further, according to the present invention, in order to control the transmittance of a mask pattern for illumination light so that a defect on the photomask can be detected, an absorbent used on the mask substrate, the material of the thin film and the material of the mask substrate are appropriately selected.

Further, in a case where the mask substrate and a phase shifter (that is, a thin film) are different in refractive index from each other, or another thin film different in refractive index from the phase shifter is sandwiched between the mask substrate and the phase shifter, the defect detecting apparatus according to the present invention is also provided with means for detecting the reflected light from the photomask, and the light and darkness distribution in the reflected light is compared with that in the transmitted light to detect a defect in a light shielding film or phase shifter.

Although various aspects of the present invention have been explained above, a defect-detecting apparatus according to the present invention can detect a defect in the phase shifter in the following manner. When coherent or partially coherent light emitted from a light source passes through a wavelength selection filter, coherent or partially coherent light having a predetermined wavelength is obtained and used as illumination light. A photomask to be inspected is locally provided with a thin transparent film for shifting the phase of the illumination light. Accordingly, when a defect is generated in the thin transparent film in such a manner that a portion of the thin transparent film is removed for some reason, a dark image is formed at the contour of the above portion (namely, a film lacking area) on the basis of the interference between light passing through the film lacking area and light passing through outside of the film lacking area. In other words, the defect detecting apparatus according to the present invention can illuminate a photomask with light which is identical with illumination light used in a projection aligner. When the light passing through the photomask is focused on an imaging device, an image of a mask pattern is formed so that the contour of the film lacking area is indicated by a dark line. By comparing the pattern image with a non-defective image or an image reconstructed from design data, the defect in the thin transparent film can be detected.

In a case where a mask substrate and a phase shifter (namely, a thin transparent film for shifting the phase of illumination light) are different in refractive index from each other, or another thin transparent film different in refractive index from the phase shifter is interposed between the mask substrate and the phase shifter, defect detection using the reflected light beam from a photomask and defect detection using the transmitted and reflected light beams from the photomask can be carried out in addition to defect detection using the transmitted light beam from the photomask.

DESCRIPTION OF THE PREFERRED EMBODIMENTS

Embodiment I

Figure 1:
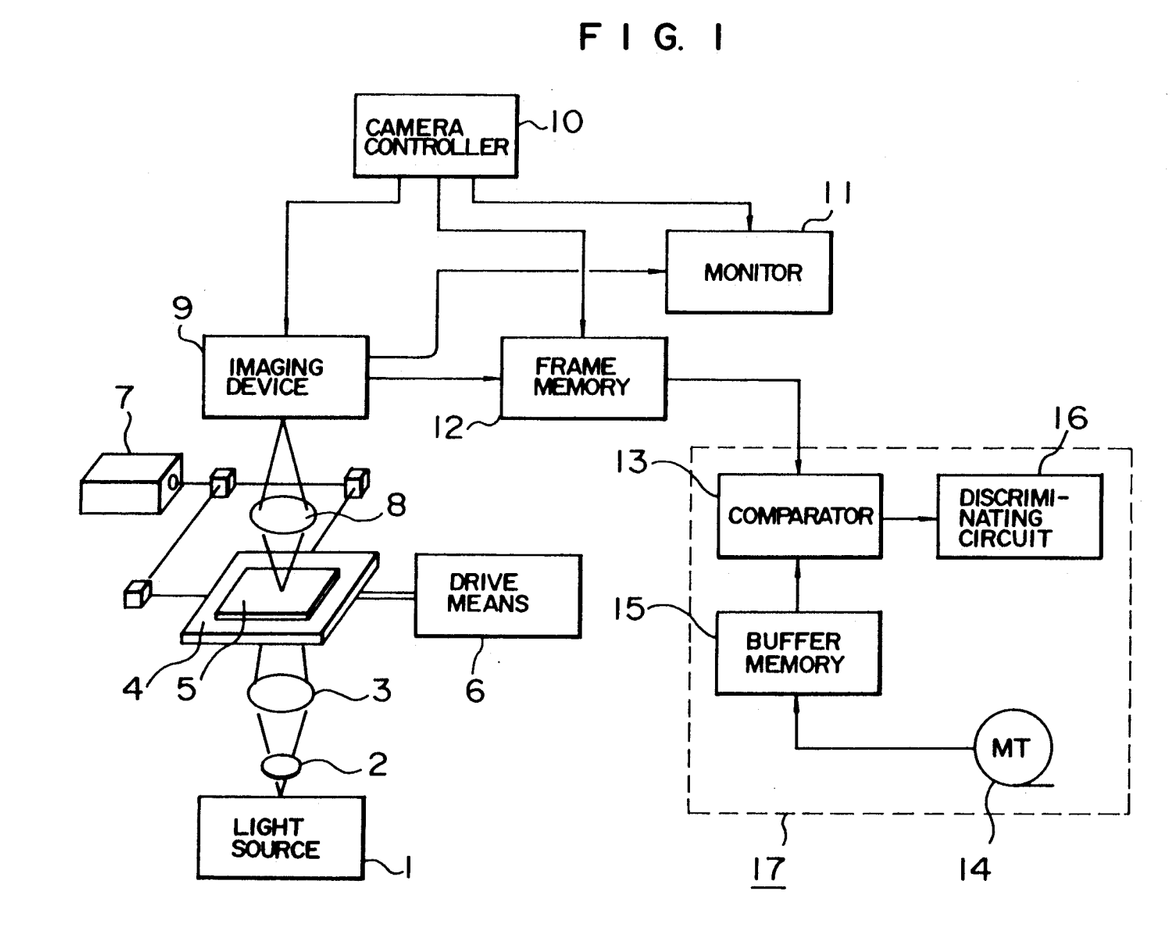
FIG. 1 is a diagram showing a first embodiment of an apparatus for detecting a defect on a photomask in accordance with the present invention.

Now, explanation will be made of a first embodiment of an apparatus for detecting a defect on a photomask in accordance with the present invention with reference to FIG. 1. Referring to FIG. 1, partially coherent light is emitted from a light source 1 which is made up of a mercury lamp and an aperture stop to be used as illumination light. The illumination light from the light source 1 passes through a wavelength selection filter 2 and a focusing lens 3, and is then incident on a photomask 5 which is fixed to a predetermined position on a stage 4. The stage 4 is moved by drive means 6, and the position of the stage 4 is precisely measured by a laser interferometer 7. The transmitted light from the photomask 5 passes through another focusing lens 8 to form an image of a mask pattern on an imaging device (that a, camera head) 9. The output signal of the imaging device 9 is sent to a comparing/discriminating circuit 17 through a frame memory 12 under control of a camera controller 10 to be compared with design data for detection of a defect on the photomask 5. The output signal of the imaging device 9 is also sent to a monitor 11 under control of the camera controller 10. The comparing/discriminating circuit 17 is made up of a magnetic tape (MT) 14, a buffer memory 15, a comparator 13 and a discriminating circuit 16. A defect on the photomask 5 can be detected in the following manner. Design data recorded on the magnetic tape 14 for forming a mask pattern is used for reconstructing a predetermined image which is temporarily stored in the buffer memory 15. Then, the contents of the frame memory 12 are compared with the contents of the buffer memory 15 by the comparator 13, and the result of comparison is sent to the discriminating circuit 16 to check whether a defect is present or not.

Figures 2A, 2B:
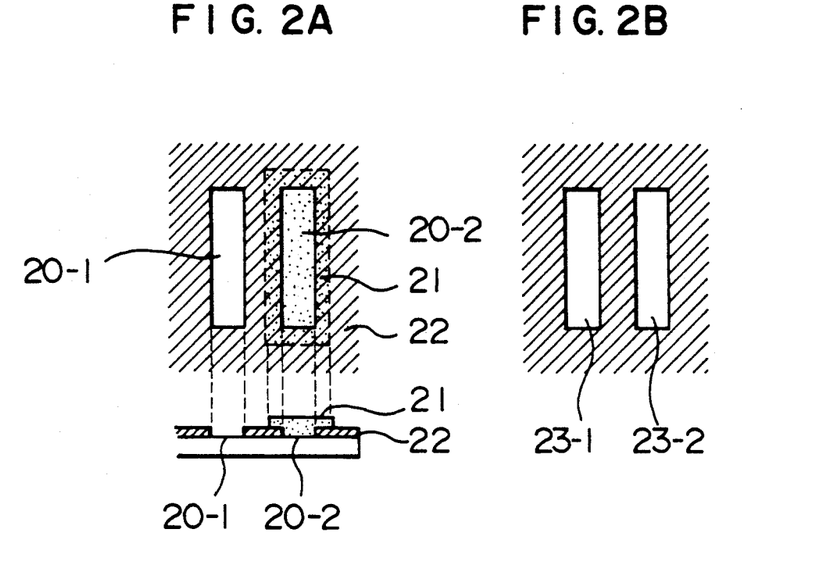
FIG. 2A is a schematic diagram showing a non-defective mask pattern.
FIG. 2B is a schematic diagram showing the detected image of the mask pattern of FIG. 2A.
Figure 3A:
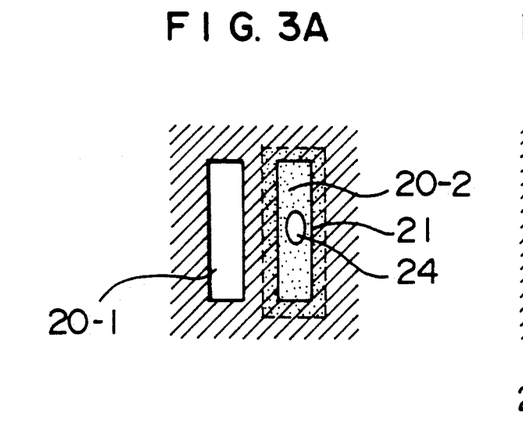
FIG. 3A is a schematic diagram showing a defective mask pattern.
Figure 3B:
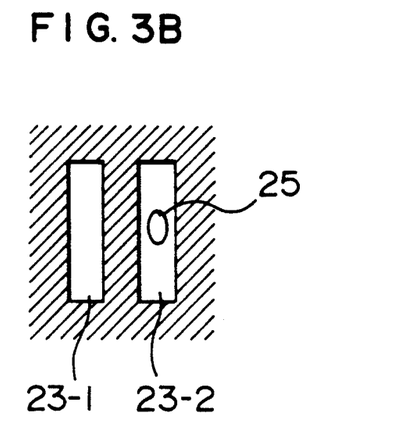
FIG. 3B is a schematic diagram showing the detected image of the mask pattern of FIG. 3A.

Referring now to FIG. 2A, let us consider a case where a light shielding area 22 of the photomask 5 includes two apertures 20-1 and 20-2 of the same size, and only the aperture 20-2 is coated with a transparent, non-defective film 21. Then, an image shown in FIG. 2B is stored in the frame memory 12. Bright portions 23-1 and 23-2 shown in FIG. 2B correspond to the apertures 20-1 and 20-2, respectively, and the portions 23-1 and 23-2 are equal in shape to each other. In a case where a part 24 of the transparent film 21 is removed as shown in FIG. 3A, an image shown in FIG. 3B is sent to the comparing/discriminating circuit 17 through the frame memory 12. As shown in FIG. 3B, a dark line 25 is formed along the contour of the film lacking part or defect 24. This is because the wavelength of the coherent or partially coherent illumination light is selected such that the transparent film 21 shifts the phase of the illumination light by a phase angle of 180°, and a dark image is formed at the contour of the film lacking part 24 on the basis of interference between light passing through, the film lacking part 24 and light passing through the transparent film 21 outside of the film lacking part 24. The defect 24 in the transparent film 21 can be detected by recognizing the dark line 25. The image of the photomask 5 can be formed on the imaging device 9 at one time. Alternatively, the illumination light is focused on the photomask 5 to form an image of a very fine area of the photomask 5 on the imaging device 9, and the photomask 5 is scanned with the focused illumination light to obtain the image of the whole of the photomask 5.

In the above explanation, the phase of the illumination light is shifted by a thin transparent film having a predetermined thickness. The phase of the illumination light can be shifted by other methods. For example, a mask substrate may be selectively etched to a predetermined depth, or the mask substrate is locally made high or low in refractive index. In either case a defect in a region which serves as a phase shifter, can be detected by the present embodiment in the form of the dark line 25 of FIG. 3B.

Embodiment II

Figure 4:
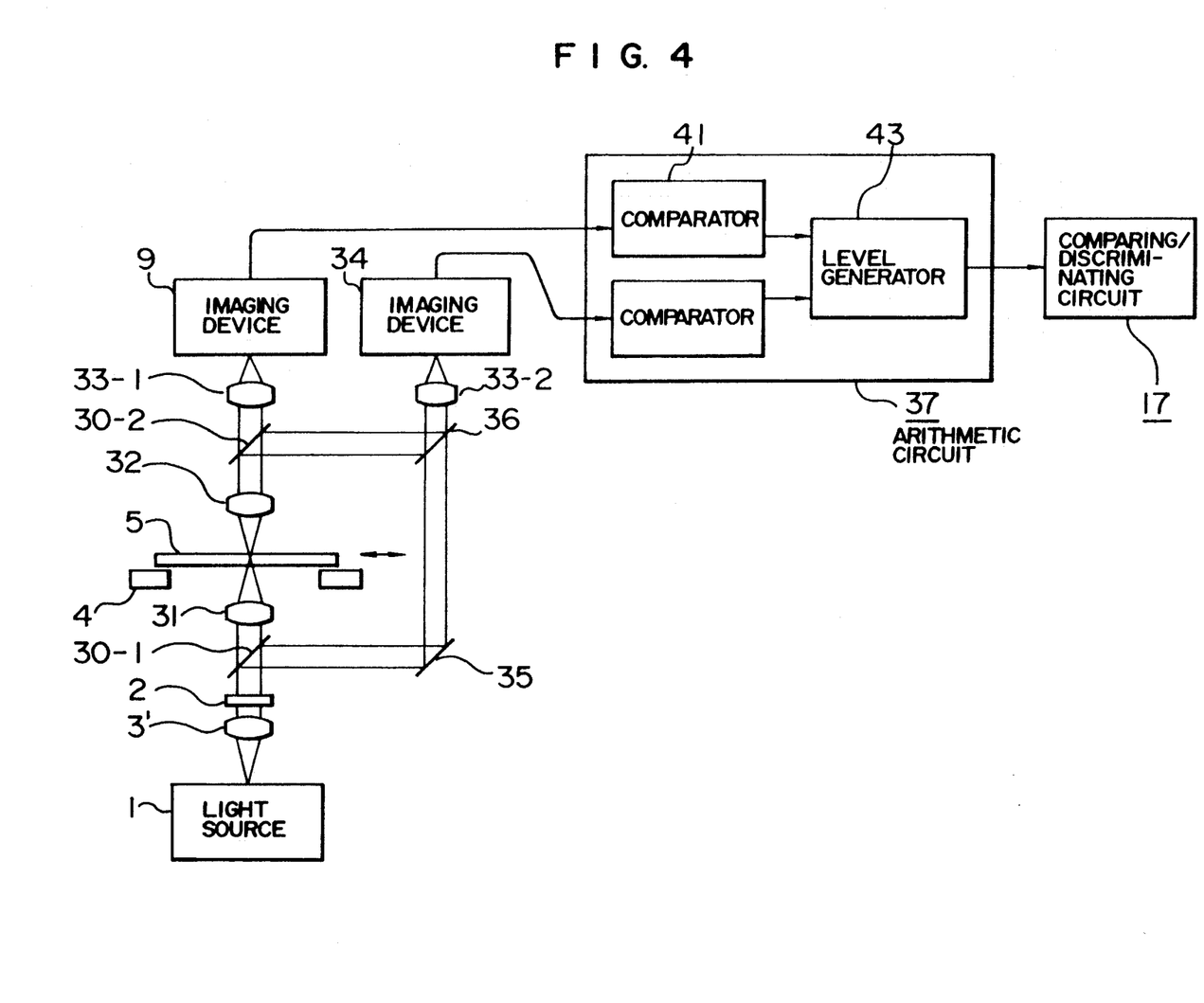
FIG. 4 is a diagram showing a second embodiment of an apparatus for detecting a defect on a photomask in accordance with the present invention in which light passing through the photomask and a reference light independent of the photomask are used for detecting the defect.

FIG. 4 shows a second embodiment of an apparatus for detecting a defect on a photomask in accordance with the present invention. According to the present embodiment, in addition to the detection of the contour of a defect in a thin transparent film serving as a phase shifter, it is determined whether a defect bringing about a phase shift of 0° is present in a light transmitting area which produces a phase shift of 180°, or vice versa. Referring to FIG. 4, the illumination light from the light source 1 passes through a collimator lens 3' and the wavelength selection filter 2. The parallel rays thus obtained are separated by a beam splitter 30-1 into two light beams, one of which is directed to an imaging device 34 through a focusing lens 33-2 without passing through the photomask 5 to be used as a reference light beam. The other light beam is focused on the photomask 5 by a focusing lens 31. The transmitted light from the photomask 5 passes through a collimator lens 32. The parallel rays thus obtained are separated by a beam splitter 30-2 into two light beams, one of which is incident on the imaging device 9 through a focusing lens 33-1. The other light beam from the beam splitter 30-2 and the reference light beam from the beam splitter 30-1 are caused to interfere. The resultant light beam thus obtained is incident on the imaging device 34. The position of the stage 4 mounted with the photomask 5 is always measured by the laser interferometer (not shown). That is, a light focusing position on the photomask 5 is always measured.

According to the optical system shown in FIG. 4, when the illumination light passing through the photomask 5 is not subjected to any phase shift, bright light is incident on each of the imaging devices 9 and 34. Let us consider a case where the photomask 5 is provided with a thin film for shifting the phase of the illumination light by a phase angle of about 180°. When each of the imaging devices 9 and 34 receives bright light, it is determined that the thin film does not exist at the light focusing position on the photomask 5. When the imaging device 9 receives bright light and the imaging device 34 receives dark light, it is determined that the thin film exists at the light focusing position on the photomask 5. When, the imaging device 9 receives dark light, it is determined that the light focusing position on the photomask lies in a light shielding area. The output signals of the imaging devices 9 and 34 are applied to an arithmetic circuit 37 which produces three levels. These levels are applied to the comparing/discriminating circuit 17 to be compared with design data. Thus, a defect in the thin film serving as a phase shifter can be detected. The arithmetic circuit 37 includes comparators 41 and 42 for converting the output signals of the imaging devices 9 and 34 into digital signals, and a level generator 43 for generating three levels in accordance with the digital signals from the comparators 41 and 42.

In a case where the phase of the light passing through the photomask fluctuates widely because of the nonuniform thickness of a mask substrate, the present embodiment may fail to detect a defect in the thin film serving as a phase shifter. However, when the photomask 5 is scanned by the focused illumination light, the time variation of transmitted light quantity due to the nonuniform thickness of the mask substrate will be far smaller than the time variation of transmitted light quantity due to the presence or absence of the thin film. Accordingly, it is possible to discriminate between a change in transmitted light quantity due to the nonuniform thickness of the mask substrate and a change in transmitted light quantity due to the thin film. In more detail, when a position on the photomask 5 where the intensity of light due to interference between the transmitted light and the reference light varies by more than a predetermined amount is detected in a scanning period, such a position represents the boundary between a light transmitting portion bringing about no phase shift and a light transmitting portion bringing about a phase shift of about 180°. Accordingly, when the arithmetic circuit 37 has a function of detecting the intensity variation of light incident on the imaging device 34 and a signal corresponding to the detected intensity variation is applied to the comparing/discriminating circuit 17 to be compared with design data, the film lacking part 24 of FIG. 3A can be detected.

Embodiment III

Figure 5:
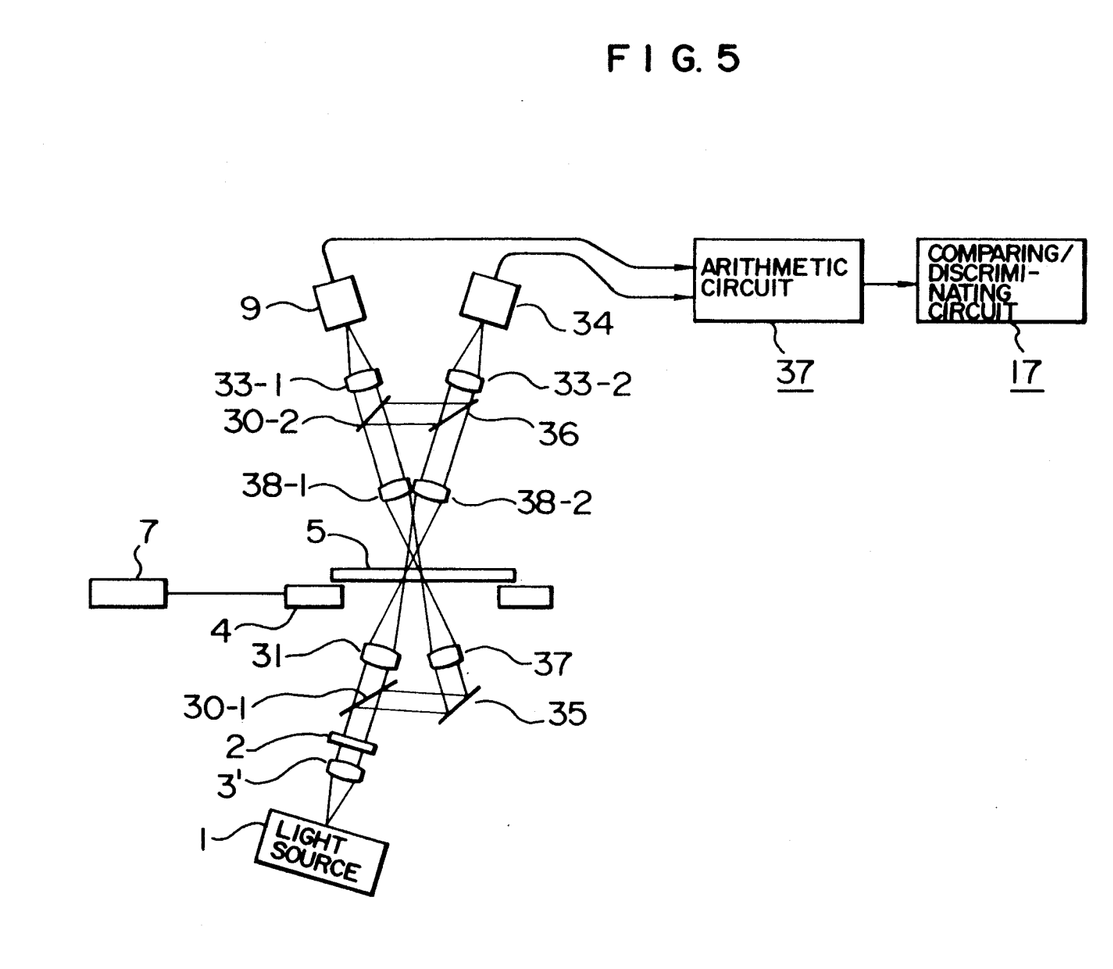
FIG. 5 is a diagram showing a third embodiment of an apparatus for detecting a defect on a photomask in accordance with the present invention in which embodiment light beams passing through adjacent points on the photomask are used for detecting the defect.

FIG. 5 shows a third embodiment of an apparatus for detecting a defect on a photomask in accordance with the present invention. In the present embodiment, as shown in FIG. 5, the illumination light is separated by the beam splitter 30-1 into two light beams, and both of the light beams pass through the photomask 5. Referring to FIG. 5, the above light beams are focused on the photomask 5 so that the light focusing positions of the light beams are spaced apart from each other by a distance of 2 to 5 μm. After having passed through the photomask 5, one of the above light beams is directed to the imaging device 34, and the other light beam is separated by the beam splitter 30-2 into two light beams. One light beam from the beam splitter 30-2 is received by the imaging device 9, and the other light beam from the beam splitter 30-2 is directed to the imaging device 34. Accordingly, light passing through one of the light focusing positions on the photomask 5 and light passing through the other light focusing position interfere, and the resultant light thus obtained is received by the imaging device 34. Thus, when the contour of a defect in a thin film (namely, phase shifter) lies between the light focusing positions on the photomask 5, the imaging device 34 receives dark light. As can be seen from the above explanation, a defective mask pattern different from design data can be detected by processing the output signals of the imaging devices 9 and 34 with the aid of the arithmetic circuit 34 and comparing/discriminating circuit 17 which have been explained in the Embodiment II.

Further, in the present embodiment, the position of the stage 4 mounted with the photomask 5 is always measured by the laser interferometer 7. Hence, the position of the defect can be precisely detected. Additionally, the light beams separated by the beam splitter 30-1 pass through light focusing positions which lie in close proximity to each other, and hence there is no fear of erroneously detecting a phase shift due to the nonuniform thickness of a mask substrate.

Further, it is not always required to make the illumination light for inspection equal in wavelength to the exposure light for projecting an image of a mask pattern on a resist film or other surfaces. In a case where the illumination light is different in wavelength from the exposure light, the intensity of the light due to interference is not equal to zero, but is far weaker than the intensity of transmitted light from the photomask 5.

Embodiment IV

Figure 6:
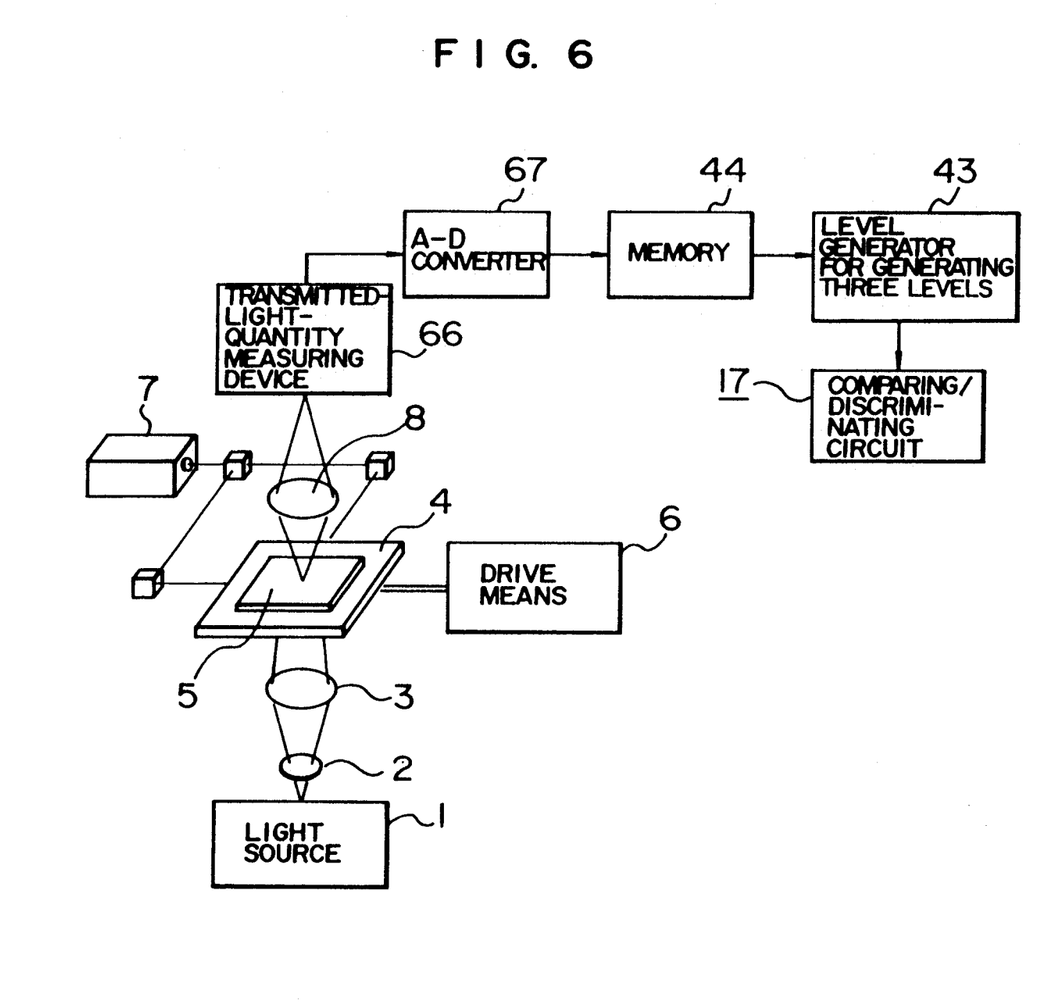
FIG. 6 is a diagram showing a fourth embodiment of an apparatus for detecting a defect on a photomask in accordance with the present invention in which embodiment the quantity of light passing through the photomask is measured to detect the defect.

FIG. 6 shows a fourth embodiment of an apparatus for detecting a defect on a photomask in accordance with the present invention. As shown in FIG. 6, the present embodiment includes the light source 1, the focusing lens 3, the stage 4 for holding the photomask 5 thereon, the focusing optical system (that is, a receiving optical system) 8, a transmitted-light-quantity measuring device 66, an A-D converter 67, a memory 44, the level generator 43 for generating three levels, the drive means 6 for driving the stage 4, and the laser interferometer 7. A xenon-mercury lamp is used as the light source 1, and light emitted from the light source 1 is incident on the filter 2. The filter 2 is selected so that light having a wavelength of 254 nm passes through the filter 2. The stage 4 has a structure that the photomask 5 can be fixed to a predetermined position on the stage 4, and is moved by the drive means 6. The position of the stage 4 is precisely measured by the laser interferometer 7. The brightness at a desired position on the photomask 5 can be measured by the receiving optical system 8 and the transmitted-light-quantity measuring device 66. A signal corresponding to a received light quantity is sent from the device 66 to the A-D converter 67 to be converted into a digital signal. The digital signal thus obtained is stored in the memory 44. The A-D converter 67 converts the input signal thereto into the digital signal in synchronism with the output signal of the laser interferometer 7 for measuring the position of the stage 4. The level generator 43 compares information from the memory 44 with three predetermined levels corresponding to a light shielding area, a light transmitting area and a phase shifting area to generate three levels. The levels thus obtained are applied to the comparing-/discriminating circuit 17 to be compared with design data. Thus, a defect on the photomask 5 can be detected.

Figure 7:
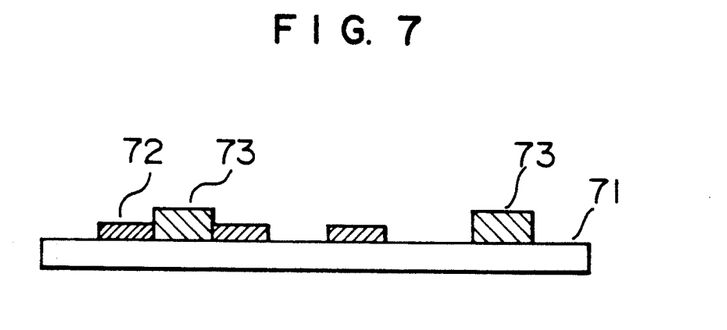
FIG. 7 shows a photomask which can be inspected by the embodiment of FIG. 6.

The photomask used in the present embodiment has a structure shown in FIG. 7. That is, the photomask includes a quartz plate 71, a chromium film 72 for shielding light, and a thin film 73 serving as a phase shifter. The thin film 73 is made of TSMR8800 (a trade name) manufactured by Tokyo Ohka Co. Ltd. Alternatively, the thin film 73 may be formed of a resist film which is made of a novolac resin other than TSMR8800. In the present embodiment, illumination light having a wavelength of 254 nm is used for detecting a defect on the photomask. In a case where the thin film 73 is made of a novolac resin, light having a wavelength less than 340 nm can be used for defect detection, since the transmittance of the thin film 73 is decreased for light having a wavelength less than 340 nm.

The thin film 73 (that is, the phase shifter) which can be inspected by the present embodiment may be formed of an SiN layer, an optical glass layer, a silicon oxide layer containing at least one of titanium, lead, tin, gold, indium, lanthanum, antimony, tantalum, yttrium, zirconium and cerium, or an organic layer containing a benzene nucleus such as a polystyrene layer. Additives such as titanium and lead act as an absorbent for light having a specified wavelength. Incidentally, light having a wavelength of 436 nm is used for projecting an image of the above photomask on a resist layer. In a case where the thin film 73 is formed of an organic layer containing a benzene nucleus, it is preferable to inspect a defect in the thin film by light having a wavelength less than 280 nm, since the transmittance of the organic layer is decreased for the above light. It is very important to select the wavelength of the illumination light for detecting a defect in the thin film 73 so that the transmittance of the thin film is decreased for the selected wavelength. Accordingly, the wavelength of the illumination light for detecting a defect in the thin film may be made longer than the wavelength of exposure light for projecting an image of the photomask on a resist layer.

The intensity distribution of transmitted light on the photomask 5 is measured by the present embodiment, and the photomask 5 is divided into a transparent area, a semi-transparent area and a light shielding area in accordance with the intensity of the transmitted light. These areas are compared by the comparing/discriminating circuit 17 with design data to detect a pin hole and a film lacking portion. That is, it is checked whether or not an area where a chromium film is to be deposited is coincident with the light shielding area, whether or not an area where a phase shifter is to be deposited is coincident with the semitransparent area, and whether or not the exposed surface area of the quartz substrate 71 (the light transmitting area without the phase shifter) is coincident with the transparent area.

The phase shifting area is transparent for the exposure light used for projecting an image of a mask pattern on a resist layer. Accordingly, the conventional defect detection method cannot discriminate between the phase shifting area and the exposed surface area of a transparent substrate. According to the present embodiment, the illumination light for detecting a defect in the phase shifter is made different in wavelength from the exposure light for projecting an image of the mask pattern on the resist film, and the material of the phase shifter is selected so that the phase shifter is semi-transparent for the defect detecting light. Thus, a defect in the phase shifter can be detected by the present embodiment. It is needless to say that the present embodiment can also detect a defect in each of the light shielding area and the exposed surface area of the mask substrate.

The present embodiment utilizes a fact that the transmittance of a phase shifter is decreased for light lying in a wavelength range Alternatively, the phase shifter may be formed of a polarizer. In this case, linearly-polarized light inclined at 45° with the plane of polarization of the polarizer is used as illumination light. Then, the chromium film intercepts the illumination light, the quantity of light passing through the polarizer is one half the quantity of the illumination light incident thereon, and the illumination light passing through the exposed surface area of the transparent substrate is scarcely absorbed by transparent substrate.

Embodiment V

Figure 8:
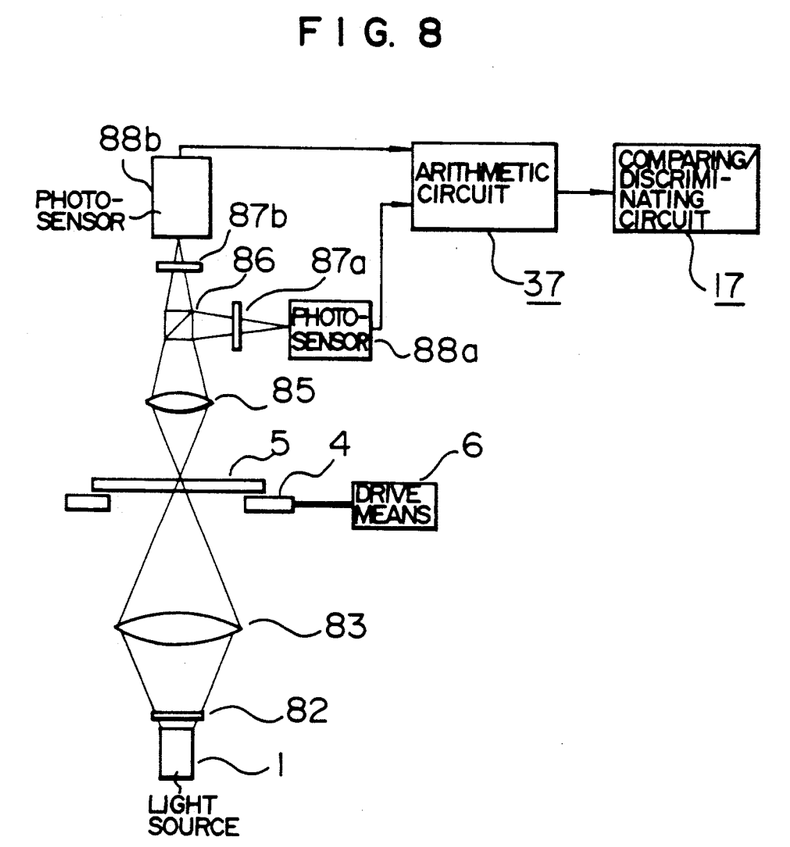
FIG. 8 is a diagram showing a fifth embodiment of an apparatus for detecting a defect on a photomask in accordance with the present invention in which the light quantities of two wavelength components passing through the photomask are measured to detect the defect.

FIG. 8 shows a fifth embodiment of an apparatus for detecting a defect on a photomask in accordance with the present invention. As shown in FIG. 8, the present embodiment includes the light source 1, a band pass filter 82, an illuminating optical system 83, the stage 4 for holding the photomask 5 thereon, a receiving optical system 85, a beam splitter 86, band pass filters 87a and 87b, photo-sensors 88a and 88b, the arithmetic circuit 37, the comparing/discriminating circuit 17, and the drive means 6 for moving the stage 4. A mercury-xenon lamp is used as the light source 1, and the filter 82 transmits only a wavelength component of 254 nm and a wavelength component of 436 nm. These wavelength components pass through the illuminating optical system 83, and are then incident on the photomask 5 which is fixed to the stage 4. As in the fourth embodiment, the photomask 5 has the structure shown in FIG. 7. The thickness of the phase shifter 73 shown in FIG. 7 is selected so that the phase shifter 73 shifts the phase of the wavelength component of 436 nm by a phase angle of $\pi$ or 180°.

Light passing through the photomask 5 is incident on the photosensors 88a and 88b through the receiving optical system 85, the beam splitter 86, and the filters 87a and 87b. The filter 87a can transmit only the wavelength component of 436 nm, and the filter 87b can transmit only the wavelength component of 254 nm. The receiving optical system 85 is disposed so that only light passing through a predetermined position in a plane on which the photomask 5 is moved, is directed to the photosensors 88a and 88b. Owing to chromatic aberration, the image formation plane for the wavelength component of 254 nm is different from the image formation plane for the wavelength component of 436 nm. Accordingly, the photosensors 88a and 88b are disposed so as to be placed on the image formation plane for the wavelength component of 436 nm and the image formation plane for the wavelength component of 254 nm, respectively. Detection signals delivered from the photosensors 88a and 88b for indicating light or darkness are sent to the arithmetic circuit 37, and three levels from the arithmetic circuit 37 are compared by the comparing/discriminating circuit 17 with design data for fabricating the photomask to detect a defective mask pattern.

Figure 9A:
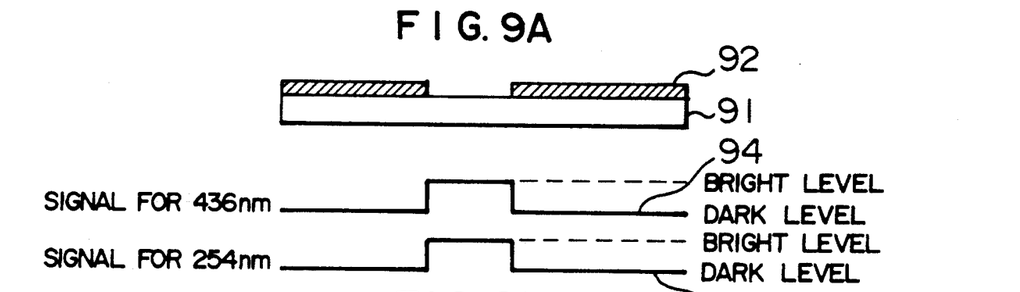
FIG. 9A shows a mask pattern having no phase-shifting film, and detection signals which are obtained by the embodiment of FIG. 8 in accordance with the mask pattern.
Figure 9B:
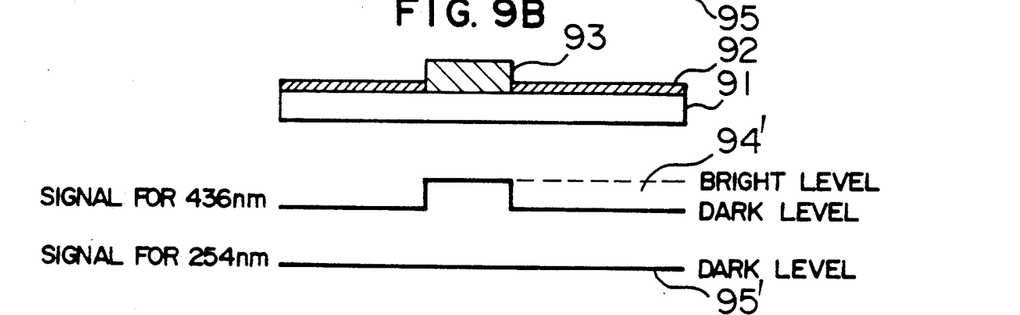
FIG. 9B shows a mask pattern having a phase-shifting area, and detection signals which are obtained by the embodiment of FIG. 8 in accordance with the mask pattern.
Figure 9C:
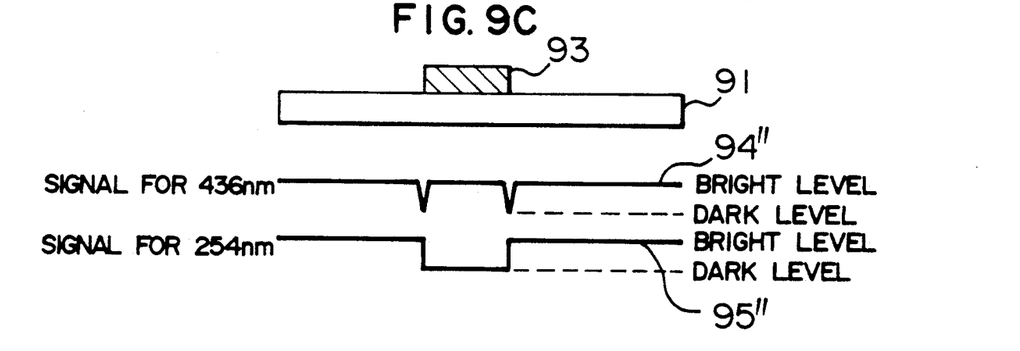
FIG. 9C shows a mask pattern having a phase shifter in a light transmitting area, and detection signals which are obtained by the embodiment of FIG. 8 in accordance with the mask pattern.

Now, the method of defect detection according to the present embodiment will be explained in detail. Referring to FIGS. 9A, 9B and 9C, reference numerals 94, 94' and 94" designate signals for the wavelength of 436 nm, and 95, 95' and 95" signals for the wavelength of 254 nm. As shown in FIG. 9A, a chromium film 92 deposited on a transparent substrate 91 does not transmit light. Further, as shown in FIG. 9B, a phase shifter 93 deposited on the substrate 91 transmits the wavelength component of 436 nm, but scarcely transmits the wavelength component of 254 nm. The transparent substrate 91, as shown in FIG. 9A, can transmit both of the above wavelength components. Further, as shown in FIG. 9C, a dark image corresponding to the boundary between the phase shifting area and the exposed surface area of the substrate is formed by the wavelength component of 436 nm.

Two photosignals corresponding to the above wavelength components are processed by the arithmetic circuit 37 in accordance with the above-mentioned situation, to discriminate among three areas, that is, among the light shielding area coated with the chromium film, the phase shifting area and the exposed surface area of the transparent substrate. These areas are compared with design data recorded on a magnetic tape to check the presence or absence of a defect and to determine the position, size and kind of the defect. Thus, various defects such as a chromium-film lacking portion in a light shielding area, an unetched chromium layer in a transparent area, a defect in the phase shifter, and the peeling of the phase shifter can be detected by the above-mentioned method. In this method, an output signal from each of the photosensors 88a and 88b is converted into a binary signal for indicating light or darkness. Accordingly, signal processing can be readily carried out, and moreover signal levels can be set with a large margin.

In the present embodiment, signals from the photomask are compared with design data recorded on a magnetic tape to detect a defect on the photomask. However, the detection of a mask defect is not limited to this method, but a defect on the photomask may be detected by a mask comparing method. That is, two photomasks having the same mask pattern are used, and corresponding positions on the photomasks are simultaneously inspected. Two signals thus obtained are compared with each other to check the presence or absence of a defect. It is to be noted that in a case where the same defect exists at corresponding positions on the photomasks, the defect cannot be detected by this method.

In the present embodiment, two wavelength components use the illuminating optical system and the receiving optical system in common and are separated from each other at a final stage. Alternatively, two wavelength components may use different illuminating optical systems and different receiving optical systems.

Embodiment VI

Now, explanation will be made of a sixth embodiment of an apparatus for detecting a defect on a photomask in accordance with the present invention with reference to FIG. 10.

Figure 10:
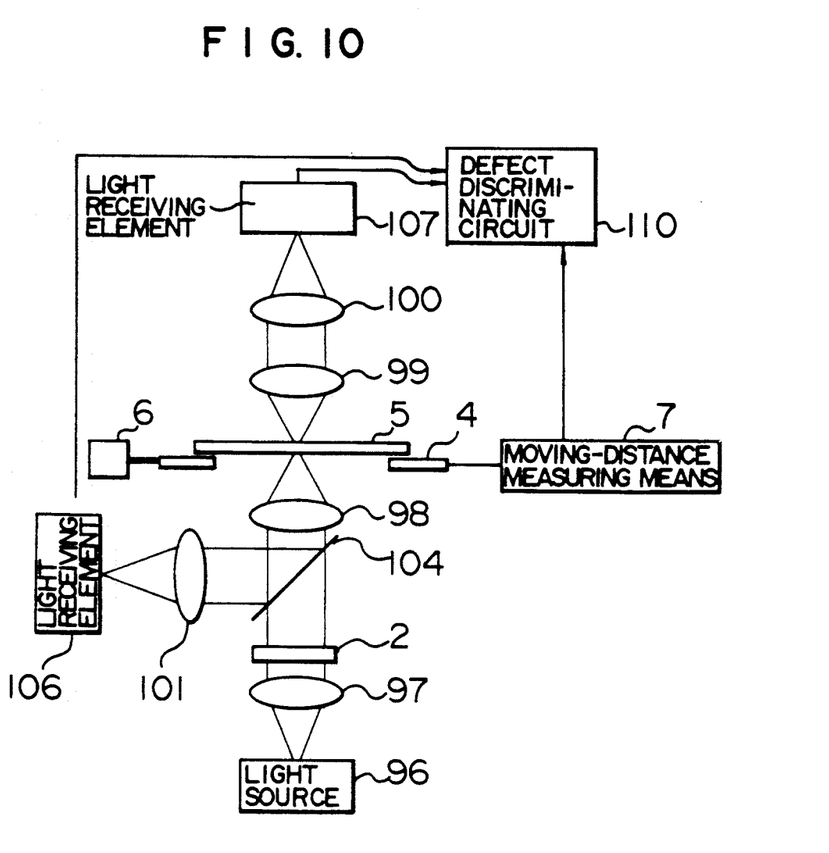
FIG. 10 is a diagram showing a sixth embodiment of an apparatus for detecting a defect on a photomask in accordance with the present invention in which the light quantities of transmitted and reflected light beams from the photomask are measured to detect the defect.

Referring to FIG. 10, illumination light which is emitted from a light source 96 and is not always required to be coherent or partially coherent light, passes through a collimator lens 97, the wavelength selection filter 2 and a focusing lens 98, and is then incident on the photomask 5 which is placed upside down. The photomask 5 is mounted on the stage 4 which is moved by the drive means 6. The position of the photomask 5 is measured by moving-distance measuring means (for example, a laser interferometer) 7. Light passing through the photomask 5 is focused on a light receiving element 107 through a collimator lens 99 and a focusing lens 100. Light reflected back from the photomask 5 is reflected from a half mirror 104, and then focused on another light receiving element 106 by a focusing lens 101. The output signals of the light receiving elements 106 and 107 are applied to a defect discriminating circuit 110 together with positional information from the moving-distance measuring means 7 and design data recorded on a magnetic tape for fabricating the photomask 5 to check the presence or absence of a defect. The discriminating circuit 110 may be formed of, for example, the comparing/discriminating circuit 17 which has been explained in EMBODIMENT I.

Figure 11:
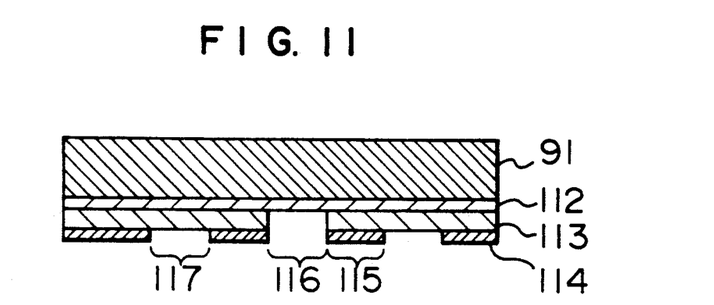
FIG. 11 is a sectional view showing a photomask which can be inspected by the embodiment of FIG. 10.

FIG. 11 shows an example of the phase-shifting photomask 5 which is inspected by the present embodiment. Referring to FIG. 11, the mask 5 is disposed so that a light shielding film 114 is placed on the under side of the mask 5 as described above in connection with FIG. 10. As shown in FIG. 11 a transparent film 112 is formed on a quartz plate 91, and a phase-shifting layer 113 is formed on the transparent film 112. The light shielding film 114 is made of chromium, and is formed on the phase-shifting layer 113. Alternatively, the light shielding film 114 may be formed between the transparent film 112 and the phase-shifting layer 113, or between the quartz plate 91 and the transparent film 112. The transparent film 112 is formed for the purpose of reflecting illumination light from the boundary between the phase-shifting layer 113 and the transparent film 112. Accordingly, in a case where the refractive index of the quartz plate 91 is only a little different from that of the phase-shifting layer 113, the transparent film 112 is very effective. In a case where the refractive index of the quartz plate 91 is greatly different from that of the phase-shifting layer 113, the transparent film 112 may be omitted, since a large amount of light can be reflected from the boundary between the quartz plate 91 and the phase-shifting layer 113.

A defect on the photomask of FIG. 11 can be detected by the present embodiment in the following manner. When illumination light is incident on a light shielding area 115, the light receiving element 106 for detecting the reflected light from the photomask 5 receives bright light, and the light receiving element 107 for detecting the transmitted light from the photomask 5 receives dark light. When the illumination light is incident on a light transmitting area 116, the light receiving element 106 receives dark light, and the light receiving element 107 receives bright light. When the illumination light is incident on a phase-shifting area 117, both of the light receiving elements 106 and 107 receive bright light. The intensity of light received by the light receiving element 106 is strongest for the reflected light from the light shielding area 115, and is weakest for the reflected light from the light transmitting area 116. The intensity of light which is reflected from the phase-shifting area 117 and received by the light receiving element 106 is intermediate between the intensity of the reflected light from the light shielding area 115 and the intensity of the reflected light from the light transmitting area 116. The wavelength of the illumination light is selected by the filter 2 in accordance with the thickness of the phase-shifting layer 113 so that a desirable amount of light is reflected from the phase-shifting area 117.

A defect on the photomask 5 is detected by comparing positional information on the photomask obtained by the moving-distance measuring means 7 and information on the state of each of the light shielding area, the light transmitting area and the phase-shifting area, with the design data recorded on the magnetic tape.

Thus, various defects such as a defect in the light shielding film 114, a defect in the phase-shifting layer 113, an unetched light-shielding film in the light transmitting area, and an unetched phase-shifting layer in the light transmitting area are accurately detected by the present embodiment.

The present embodiment may be modified, provided that the modified version is provided with means for detecting both of the transmitted light from the photomask and the reflected light therefrom, and means for discriminating among three areas (that is, the light shielding area, the light transmitting area and the phase-shifting area).

We claim:

1. A method of detecting a defect on a phase-shifting mask including a thin transparent film and a thin-light-shielding film, the method comprising the steps of:
    illuminating the phase-shifting mask with light including a predetermined wavelength component such that the light passes through the phase-shifting mask;
    detecting bright and dark information from the predetermined wavelength component; and
    detecting separately whether or not the thin transparent film is present on the phase-shifting mask and whether or not the thin light-shielding film is present on the phase-shifting mask on the basis of the bright and dark information.

2. A method according to claim 1, wherein the thin transparent film has a low transmittance for the predetermined wavelength component, and wherein the phase-shifting mask further includes a transparent substrate having a high transmittance for the predetermined wavelength component.

3. A method according to claim 2, wherein the predetermined wavelength component has a wavelength less than 340 nm.

4. A method according to claim 2, wherein the predetermined wavelength component has a wavelength less than 280 nm.

5. An apparatus for detecting a defect on a phase-shifting mask comprising:
    illuminating means for generating light;
    first beam-splitting means for splitting the light from the illuminating means into first and second light beams and for illuminating the phase-shifting mask with the first and second light beams such that the first and second light beams pass through the phase-shifting mask;
    interfering means for causing light from the first light beam to interfere with light from the second light beam after the first and second light beams have passed through the phase-shifting mask to produce an interference light beam;
    detecting means for detecting at least the interference light beam; and
    processing means for detecting a defect on the phase-shifting mask based on at least the interference light beam detected by the detecting means.

6. A method according to claim 5, wherein the detecting means includes a first detecting element and a second detecting element, wherein the interfering means includes second beam-splitting means for splitting the first light beam into third and fourth light beams after the first light beam has passed through the phase-shifting mask, and means for causing the fourth light beam to interfere with the second light beam after the second light beam has passed through the phase-shifting mask to produce the interference light beam, and wherein the third light beam is incident on the first detecting element and the interference light beam is incident on the second detecting element.

7. A method according to claim 6, wherein the first beam-splitting means illuminates the phase-shifting mask with the first and second light beams such that the first and second light beams pass through the phase-shifting mask at locations which are in close proximity to each other.

8. A method according to claim 5, wherein the phase-shifting mask includes phase-shifting means for shifting a phase of light in the first and second light beams by a phase angle substantially equal to 180° when the first and second light beams pass through the phase-shifting mask.

9. An apparatus for detecting a defect on a phase-shifting mask including a light shielding area, a semi-transparent area, and a transparent area, the apparatus comprising:
illuminating means for illuminating the phase-shifting mask with light having a predetermined wavelength such that the light passes through the phase-shifting mask;
detecting means for detecting the light passing through the phase-shifting mask; and
detecting means for discriminating between the light-shield area, the semi-transparent area, and the transparent area of the phase-shifting mask on the basis of the light detected by the detecting means.

10. An apparatus according to claim 9, wherein the predetermined wavelength is less than 340 nm.

11. An apparatus according to claim 9, wherein the predetermined wavelength is less than 280 nm.

12. An apparatus for detecting a defect on a phase-shifting mask comprising:
illuminating means for generating light including a first wavelength component and a second wavelength component;
a first filter for extracting the first wavelength component and the second wavelength component from the light generated by the illuminating means, the extracted first wavelength component and the extracted second wavelength component constituting extracted light, and for illuminating the phase-shifting mask with the extracted light such that the extracted light passes through the phase-shifting mask;
beam-splitting means for splitting the extracted light passing through the phase-shifting mask into a first light beam and a second light beam each including the first wavelength component and the second wavelength component;
a second filter for extracting the first wavelength component from the first light beam;
a third filter for extracting the second wavelength component from the second light beam;
first detecting means for detecting the first wavelength component extracted by the second filter to produce a first detection signal;
second detecting means for detecting the second wavelength component extracted by the third filter to produce a second detection signal; and
comparing means for comparing the first detection signal with the second detection signal to detect a defect on the phase-shifting mask.

13. An apparatus according to claim 12, wherein the phase-shifting mask includes a transparent substrate, and a thin transparent film formed on the transparent substrate and serving as a phase shifter, and wherein a transmittance of the transparent substrate with the thin transparent film formed thereon for the second wavelength component is different from a transmittance of the transparent substrate without the thin transparent film formed thereon for the second wavelength component.

14. An apparatus according to claim 12, wherein the phase-shifting mask includes a transparent substrate, and a thin film formed on the transparent substrate and serving as a phase shifter, and wherein the thin film is transparent to the first wavelength component and includes an absorbent for absorbing the second wavelength component.

15. An apparatus according to claim 12, wherein the second wavelength component has a wavelength less than 340 nm.

16. An apparatus according to claim 12, wherein the second wavelength has a wavelength less than 280 nm.

17. A method of detecting a defect on a phase-shifting mask including a light-transmitting area, and a transparent film area at which a transparent film is formed, the method comprising the steps of:
illuminating the phase-shifting mask with light such that a portion of the light is reflected from the light transmitting area at a relatively week intensity and is reflected from the transparent film area at a relatively strong intensity, and another portion of the light is transmitted through the light transmitting area and the transparent film area at substantially equal intensities;
detecting the reflected light and the transmitted light;
discriminating between the light transmitting area and the transparent film area on the basis of the detected reflected and transmitted light and the difference between the intensity of the light reflected from the light transmitting area and the intensity of the light reflected from the transparent film area; and
detecting a defect on the phase-shifting mask by comparing design pattern data for the phase-shifting mask with a result of the discriminating step.

18. An apparatus for detecting a defect on a phase-shifting mask including an auxiliary film formed on an entire surface of the phase shifting mask, the apparatus comprising:
illuminating means for illuminating the phase-shifting mask with light such that a portion of the light is reflected form the phase-shifting mask and another portion of the light is transmitted through the phase-shifting mask;
first detecting means for detecting the transmitted light to produce a first detection signal;
second detecting means for detecting the reflected light to produce a second detection signal; and
comparing means for comparing design pattern data for the phase-shifting mask with data generated from the first detection signal and the second detection signal.

* * * * *